(12) United States Patent
Krüger et al.

(10) Patent No.: US 7,770,580 B2
(45) Date of Patent: Aug. 10, 2010

(54) DEVICE AND METHOD FOR RESPIRATING A PATIENT BY MEANS OF HIGH-FREQUENCY VENTILATION

(75) Inventors: Thomas Krüger, Reinfeld (DE); Tobias Glaw, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 453 days.

(21) Appl. No.: 11/840,551

(22) Filed: Aug. 17, 2007

(65) Prior Publication Data

US 2008/0087284 A1 Apr. 17, 2008

(30) Foreign Application Priority Data

Oct. 14, 2006 (DE) .................. 10 2006 048 680

(51) Int. Cl.
*A61M 11/00* (2006.01)
(52) U.S. Cl. ............................ 128/204.21; 128/204.23; 128/204.18

(58) Field of Classification Search ............ 128/200.24, 128/204.18, 204.21, 204.23, 204.22, 205.23
See application file for complete search history.

(56) References Cited

U.S. PATENT DOCUMENTS

| 5,555,880 | A | 9/1996 | Winter et al. | |
|---|---|---|---|---|
| 7,121,277 | B2 * | 10/2006 | Strom | 128/204.18 |
| 2007/0215154 | A1 * | 9/2007 | Borrello | 128/204.21 |

* cited by examiner

*Primary Examiner*—Steven O Douglas
(74) *Attorney, Agent, or Firm*—McGlew and Tuttle, P.C.

(57) ABSTRACT

A device is provided for respirating a patient by means of high-frequency ventilation, which has at least one device for setting a desired tidal volume by a user, and which has at least one regulating device for regulating an amplitude of the respiration pressure and/or at least one regulating device for regulating the oscillation frequency on the basis of the tidal volume determined. A corresponding method is provided for regulating a device for respirating a patient by high-frequency ventilation and a method is provided for respirating a patient.

22 Claims, 6 Drawing Sheets

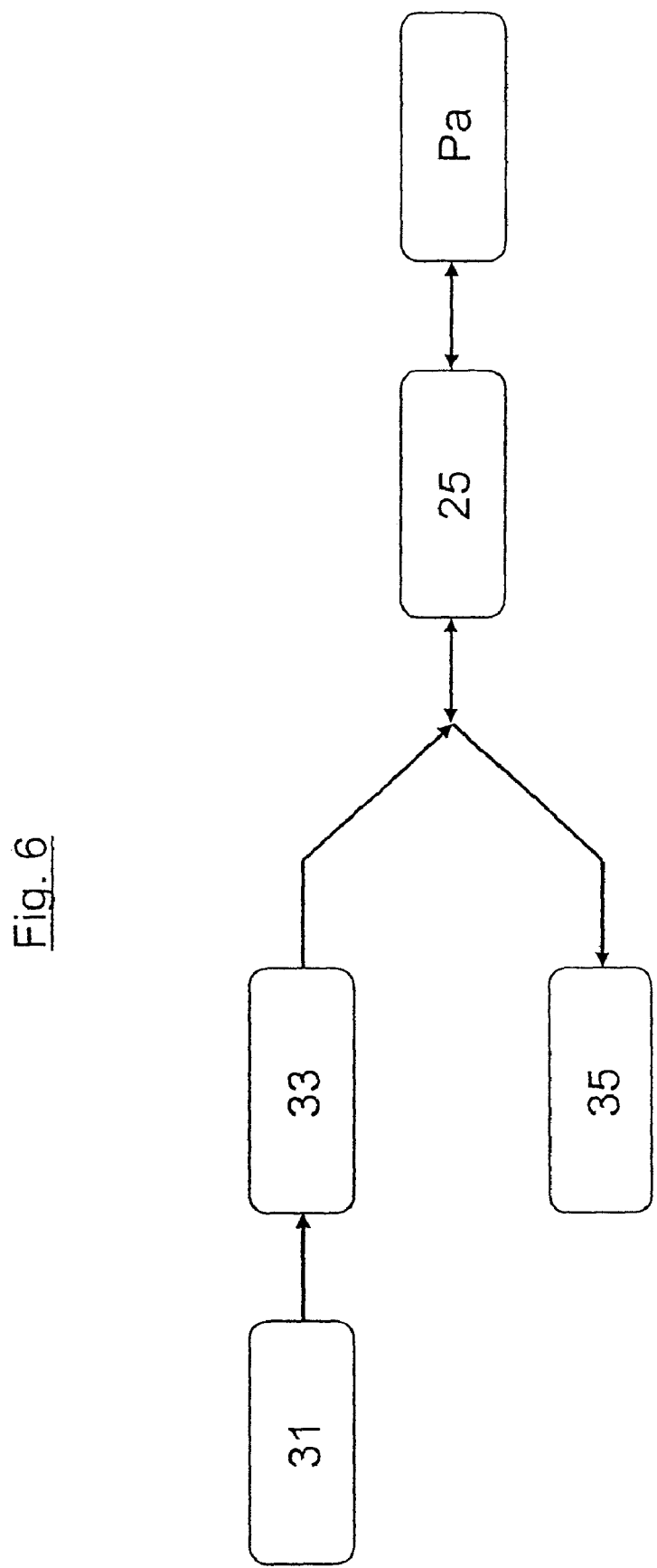

DEVICE AND METHOD FOR RESPIRATING A PATIENT BY MEANS OF HIGH-FREQUENCY VENTILATION

CROSS REFERENCE TO RELATED APPLICATIONS

This application claims the benefit of priority under 35 U.S.C. §119 of German Patent Application DE 10 2006 048 680.3 filed Oct. 14, 2006, the entire contents of which are incorporated herein by reference.

FIELD OF THE INVENTION

The present invention pertains to a device for respirating a patient by means of high-frequency ventilation (also known as respiration) with at least one high-frequency generator for applying a tidal volume with a respiration pressure and with an oscillation frequency and at least one device for determining a tidal volume applied to the patient. The invention further relates to a method for regulating a device for respirating a patient as well as to a method for respirating a patient.

BACKGROUND OF THE INVENTION

High-frequency ventilation is a respiration therapy which has proved successful especially when respirating neonatal patients. Respiration is carried out in high-frequency ventilation at frequencies of 5-50 Hz or higher, usually as an active support during inspiration and expiration and with a respiration volume that is smaller than, equal to or only slightly larger than the dead space volume. High-frequency ventilation is characterized essentially by the mean pressure (MAP—mean airway pressure), the oscillation frequency and the amplitude (A) of the positive pressure respiration. These characteristics can be found in a pressure (P)-vs.-time (t) diagram.

Among other things, piston oscillators, are known from practice for generating the oscillation frequency necessary for the high-frequency ventilation. They excite the air column in the respiration tubes by means of a rapidly moving cylinder piston. The fresh gas supply is guaranteed by a bias flow system. The oscillations are generated by means of loudspeakers in devices of another design. Fresh gas is added via bias flow in this case as well.

The high-frequency generators known from practice also include so-called flow interrupters. They interrupt the gas flow to the patient at a high frequency and generate an "oscillation" in this manner. The inspiratory gas flow can be interrupted for this by means of a valve or a valve bank, but it is also possible to apply a high constant inspiratory flow and to generate the oscillation by rapidly opening and closing the expiration valve. A jet venturi system (ejector) acting during expiration guarantees active expiration. The necessary "oscillations" can also be brought about by means of a flow cycled according to the inspiration and with an expiration valve operating in antiphase as well as with an ejector, which permits active expiration, and with other methods and devices as well.

A respirator based on high-frequency ventilation is known from U.S. Pat. No. 5,555,880 A. The operator of the device disclosed there or the physician in charge can set the oscillation frequency and the amplitude of the respiration pressure such that the desired tidal volume is approximately applied and a ventilation that is desirable for the patient will thus take place. The set values and the tidal volume that becomes indirectly established herefrom are adapted by the physician in charge manually in case of deviations of the blood gases from target ranges.

The drawback of this prior-art system is that adjustment of the parameters set is necessary even in case of minor changes in the properties of the system, such as changes in the resistance and the compliance of the airways and the lungs of the patient, in case of accumulation of secretion in the airways, in case of changes in the compliance of the tube system or the like. Continuous monitoring of the tidal volume by the physician in charge is therefore absolutely necessary.

The drawback of the device known from U.S. Pat. No. 5,555,880 A is, moreover, that a tidal volume cannot be set directly on the device, but it can be set only indirectly via the combination of other set values such as oscillation frequency and pressure amplitude.

SUMMARY OF THE INVENTION

The object of the present invention is therefore to provide a device for respirating a patient by means of high-frequency ventilation while avoiding or diminishing at least some of the above-mentioned drawbacks. Furthermore, it is a goal of the present invention is to provide a corresponding method. Moreover, a method for ventilating a patient is provided.

Thus, the device according to the present invention for respirating a patient by means of high-frequency ventilation has at least one high-frequency generator for applying a tidal volume under a respiration pressure and with an oscillation frequency. The high-frequency generator may be a generator of one of the above-mentioned types (such as piston oscillators, loudspeakers and so-called flow interrupters) or of any other type.

The device has, furthermore, at least one means for determining a tidal volume applied to the patient. This means may be designed as a sufficiently fast flow sensor, which measures the flow that is applied to the patient. To determine the tidal volume applied during one oscillation, the flow value measured by means of this flow sensor can be integrated. A possibly developing leakage flow can likewise be taken into account when determining the tidal volume.

The device has, furthermore, at least one means for setting a desired tidal volume by the user or the physician in charge. This desired tidal volume thus corresponds to a set point of the tidal volume desired by the physician. Unlike in the state of the art, the desired tidal volume can therefore be set directly on the device by means of this means. It is therefore not necessary to perform a setting of the tidal volume, which setting is only indirect and is therefore subject to uncertainties, by setting the pressure amplitude and the oscillation frequency.

The device according to the present invention has, furthermore, a regulating means for regulating an amplitude of the respiration pressure and/or at least one regulating means for regulating the oscillation frequency on the basis of the tidal volume determined. It is thus advantageously possible according to the present invention to regulate the pressure amplitude and/or the oscillation frequency in a suitable manner in an automated manner and thus without any necessary intervention on the part of the physician in case of a deviation from the tidal volume, which is determined, i.e., applied to the patient, and the set, i.e., desired tidal volume, in a suitable manner such that the applied tidal volume increases or decreases in the direction of the value of the desired tidal volume.

In case of a deviation of the determined tidal volume from the desired tidal volume, a new value can be set for the amplitude to be changed, for example, by means of a simple linear ratio calculation:

$$\frac{\text{Amplitude\_new}}{\text{Tidal volume\_set}} = \frac{\text{Amplitude\_old}}{\text{Tidal volume\_determined}} \quad (1)$$

It appears from the simple linear ratio calculation (1) between the amplitude or pressure amplitude and the tidal volume, which was presented above, that the greater the deviation between the determined tidal volume and the desired tidal volume, the greater is also the change in the pressure amplitude.

If the initial frequency is set by the physician as a constant frequency, no automatic adaptation of the frequency takes place. This may also be provided for in any desired embodiment according to the present invention regardless of the other features of such an embodiment.

Therefore, unlike in devices known from the state of the art, it is not necessary according to the present invention for the physician or the care provider of the patient being respirated to monitor the value of tidal volume applied. As a result, the effort needed for monitoring the respiration by the physician decreases in case of the use of the device according to the present invention, as a result of which time and costs can advantageously be saved.

Moreover, the device according to the present invention responds automatically to the changes in the system, as they were described above and which would lead to inadvertent changes in the tidal volume applied without regulation. This also contributes to a reduction of the effort needed for monitoring the respiration by the physician, as a result of which time and costs can advantageously be saved.

Another advantage of the use of the device according to the present invention is the more precise and more rapid setting, monitoring and correction of the applied tidal volume, which is made possible hereby, compared to the hitherto known specifications discussed above. Due to the fact that a constant tidal volume is made available and maintained, which is made possible hereby according to the present invention for the first time ever, more constant ventilation is also possible, for the first time ever, while avoiding disadvantageous pressure peaks due to delayed adjustment of respiration parameters. In addition, respiration by means of the device according to the present invention makes it possible to achieve and make available more stable blood gases of the patient and it advantageously contributes to the avoidance of hypoventilation and hyperventilation of the patient with corresponding adverse clinical effects.

Thus, provisions are made in a preferred embodiment for the desired tidal volume to be able to be set by means of the regulating means for regulating the oscillation frequency such that the product of the second power of the tidal volume and the oscillation frequency remains constant. The abovementioned product is a transport coefficient, which is directly proportional to the carbon dioxide ($CO_2$) partial pressure and from which an increase or decrease in the quantity of $CO_2$ that is expired from the lungs per unit of time of respiration or leaves the lungs can be inferred. In other words, this means that when an initial oscillation frequency $f_{init}$ drops to a new, lower oscillation frequency $f_{new}$, the corrected tidal volume $VT_{new}$ shall relate to the set tidal volume $VT_{init}$ that occurred before the frequency change as follows:

$$VT_{new} = \sqrt{\frac{VT_{init}^2 \cdot f_{init}}{f_{new}}} . \quad (2)$$

Reduction of the oscillation frequency from $f_{init}$ to $f_{new}$, which is carried out at a tidal volume that is determined to be too low, makes possible a longer diffusion time for the oxygen present in the breathing gas and contributes to better respiration of the patient. Moreover, more time is available for the inspiration, and more breathing gas can therefore be introduced into the lungs. Improved $CO_2$ expiration is achieved as well. This adaptation is advantageously performed according to the present invention by means of the regulating means for the oscillation frequency of the respirator. It is noted that the transport coefficient for $CO_2$, which is obtained from the second power of the tidal volume multiplied by the oscillation frequency, does not have to remain strictly constant. Maintaining this transport coefficient at an approximately constant value is sufficient according to the present invention.

In a preferred embodiment of the present invention, the device according to the present invention has at least one means for setting a maximum value for the pressure amplitude of respiration, regulation of the oscillation frequency taking place only after the amplitude has been raised to the set maximum value. In this embodiment according to the present invention, the oscillation frequency is therefore adapted for correcting a tidal volume deviating from the desired tidal volume only when adaptation of the amplitude of the respiration pressure has already taken place for the same purpose—provisions being made here for the maximum value to be set for the pressure amplitude or possibly having already been reached—and there still is a need for regulating the tidal volume.

It is possible according to the present invention that due to a change in the oscillation frequency and the consequently also necessary change in the tidal volume that becomes newly established for maintaining the $CO_2$ transport coefficient at a constant value, the tidal volume will be, at least temporarily, higher than the value set—desired—by the physician. A corresponding alarm or warning can be generated in this case. An alarm can, furthermore, be triggered when the desired tidal volume cannot be applied or reached because the maximum allowable amplitude has already been reached (at least for a certain period of time) and the frequency must not be changed or the minimum necessary frequency is set.

Provisions are made in yet another preferred embodiment for waiting for a sufficient period of time after any change either in the oscillation frequency or the pressure amplitude before further changes are carried out. This period of time may be, for example, a complete oscillation, i.e., at least one oscillation of the pressure curve—or a multiple thereof. It is ensured in this manner that the system operates with the smallest possible amount of oscillations and values such as the tidal volume can advantageously be determined at an especially high accuracy.

In another preferred embodiment according to the present invention, the device according to the present invention has at least one means for regulating the oscillation frequency and/or the amplitude of the respiration pressure, by means of which a rate of change during the change in the oscillation frequency and/or the amplitude of the respiration pressure can be limited.

This embodiment is advantageously characterized in that, e.g., an artefact formation, which could compromise, for example, the accurate determination of the tidal volume, is reduced. In addition, the effect of an artefact, which develops, for example, due to the patient coughing, during which there is an especially high but short tidal volume, is reduced. In this embodiment, the system certainly has the time necessary to return again to an equilibrium or steady state after initial changes before further necessary changes are possibly carried out.

In yet another preferred embodiment according to the present invention, the device according to the present invention has a means for checking since when the set maximum value has been set for the amplitude. This embodiment is characterized in that a change in frequency is not carried out each time the pressure limitation is reached, but only when it was recognized by checking that the pressure limitation has been in effect for a sufficiently long time and it is ensured as a result that the desired tidal volume cannot be reached at the currently set oscillation frequency. The possible generation of oscillations based on only temporary pressure limitations can therefore be effectively counteracted. Furthermore, an unnecessary frequency reduction can be prevented from occurring. A frequency reduction is carried out in this embodiment only when this is really necessary.

In another preferred embodiment according to the present invention, the flow sensor may be provided on the patient side of the Y piece or in another manner adjacent to this regardless of the other features of this embodiment.

The object according to the present invention is also accomplished by the combination of the features of the method for regulating a device for respirating a patient as well as by the method for respirating a patient. Since the same advantages as those described above are achieved in full measure by means of the method for regulating a device for respirating a patient as well as the method for respirating a patient, reference is expressly made here to the above discussion of these methods to avoid repetitions.

The present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6 is a schematic simplified view of a respirator in an embodiment according to the present invention.

DESCRIPTION OF THE PREFERRED EMBODIMENTS

Figure 1:
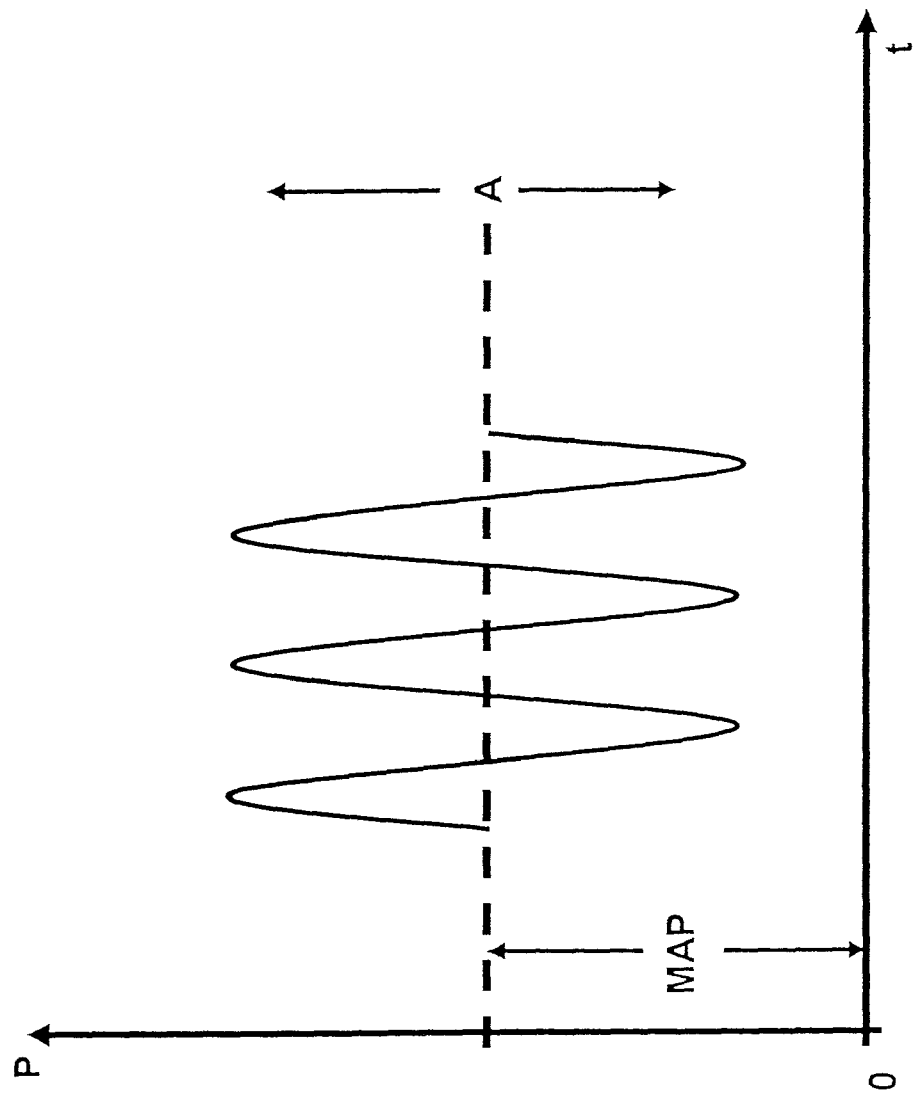
FIG. 1 is a diagram of characteristics of the high-frequency ventilation showing the pressure-vs.-time.

Referring to the drawings in particular, FIG. 1 shows a pressure-vs.-time diagram with characteristic values of the high-frequency ventilation, namely, the mean airway pressure MAP, and the amplitude A and the respiration rate that can be determined from FIG. 1 on the basis of the number of oscillations of the pressure curve over time.

Figure 2:
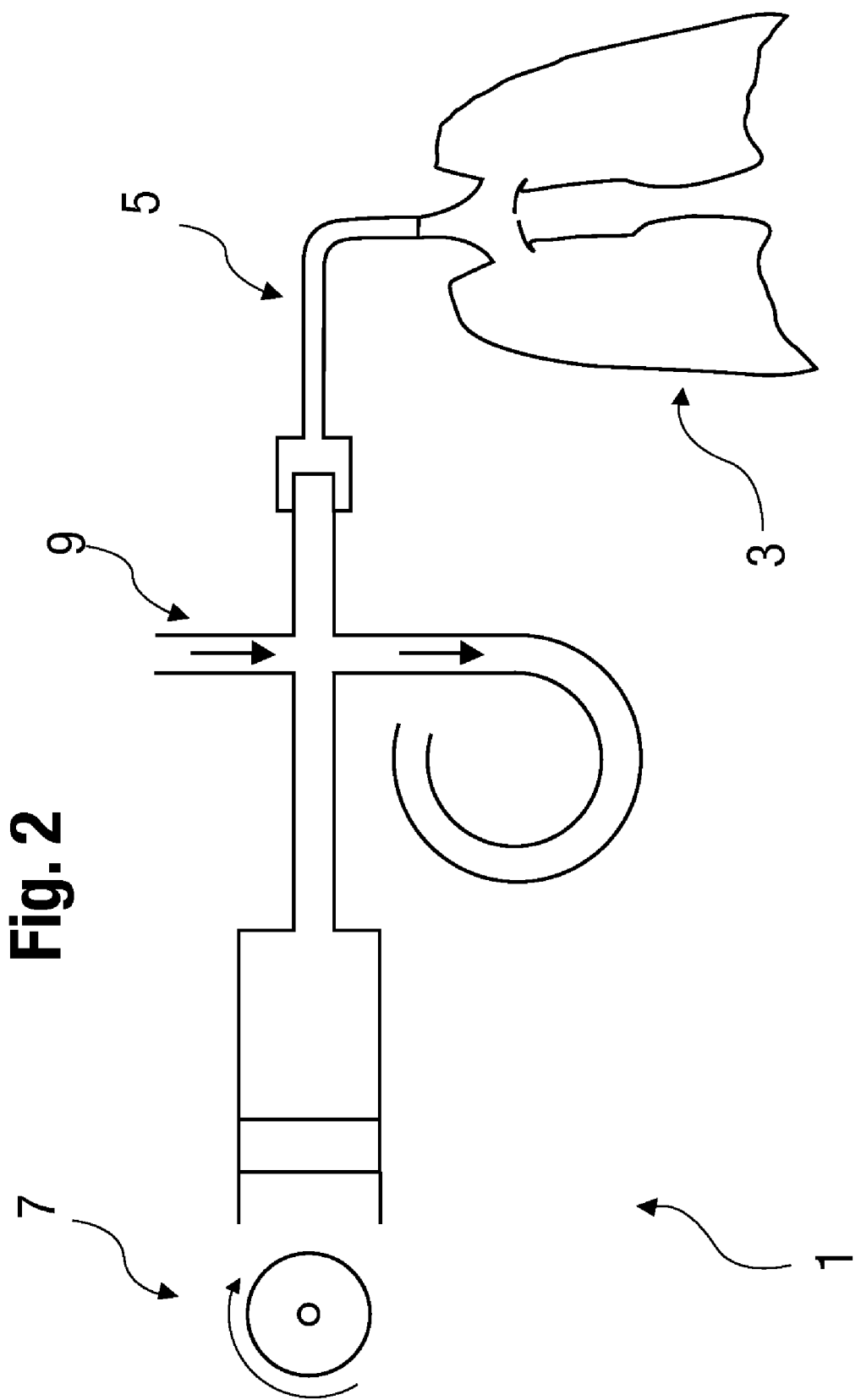
FIG. 2 is a schematic simplified view of a device for generating high-frequency oscillations for respirating a patient.

FIG. 2 shows a schematic simplified view of a device 1 for generating high-frequency oscillations for respirating a patient, which can also be used to carry out the present invention. FIG. 2 shows the lungs 3 of a patient, which are ventilated via a breathing gas line 5 with breathing gas during high-frequency respiration. The high-frequency ventilation is carried out to a considerable extent by an oscillating piston 7. FIG. 2 shows, furthermore, a fresh gas supply to the breathing line 5 by means of a bias flow 9.

Figure 3:
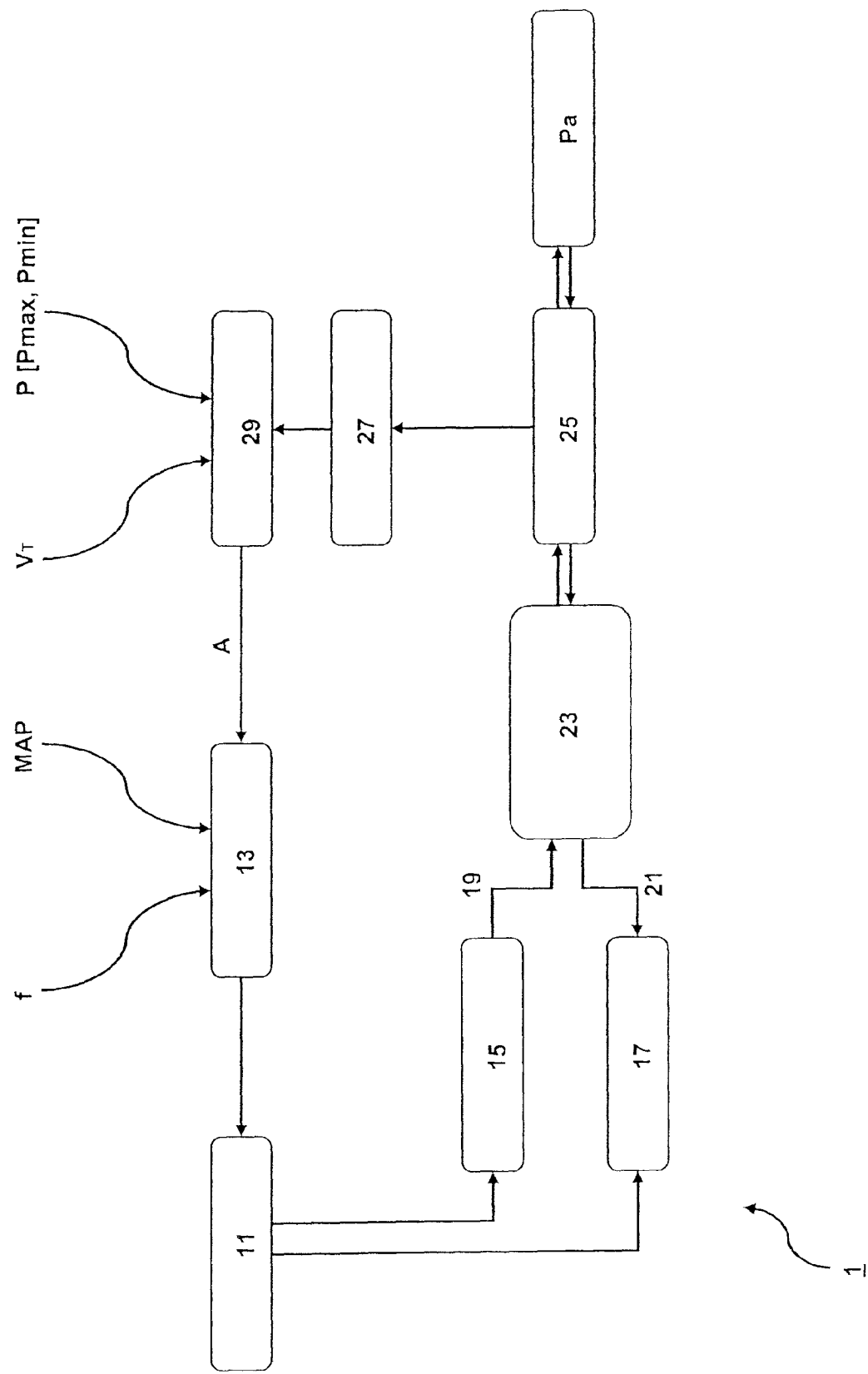
FIG. 3 is a schematic view showing a device according to the present invention.

FIG. 3 shows, likewise in a schematic simplified form, the design of a preferred embodiment of the device 1 according to the present invention, which has a pressure and flow regulator 11 and a high-frequency generator 13. A frequency f as well as a mean pressure MAP can be set by the physician as set points on the high-frequency generator 13. These set values are sent to the pressure and flow regulator 11, which will then send suitable setting values to a flow source 15 which is present in the device and has an inspiration valve and to an expiration valve 17, which is likewise present in the device 1 and has an ejector. Both the flow source 15 and the expiration valve 17 are connected to a Y piece 23 of the device 1 via an inspiration tube 19 and an expiration tube 21. A flow sensor 25, through which an inspiration and expiration gas flows, which is fed to a patient Pa by the device 1, is provided in the device 1 adjacent to the Y piece 23. The measured flow value measured by the flow sensor 25 is fed to a volume integrator 27, which calculates an actual value of the tidal volume and the tidal volume applied and sends the result of this calculation to a programmed volume guaranty algorithm 29 or to a corresponding regulating means. The algorithm 29, by means of which a guaranteed volume is ensured during high-frequency ventilation, acts on the high-frequency generator 13 in such a way that the pressure amplitude A generated by the high-frequency generator is changed corresponding to a difference between the desired tidal volume and the tidal volume determined by means of the flow sensor 25 or the volume integrator 27.

FIG. 3 shows, furthermore, that a set value for a desired tidal volume VT as well as a permissible pressure range P[Pmax, Pmin] can be set by the physician or the manufacturer in the algorithm 29. Likewise, a maximum and a minimum, which are set by the physician or the manufacturer of the device, can be set for the frequency.

Figure 4:
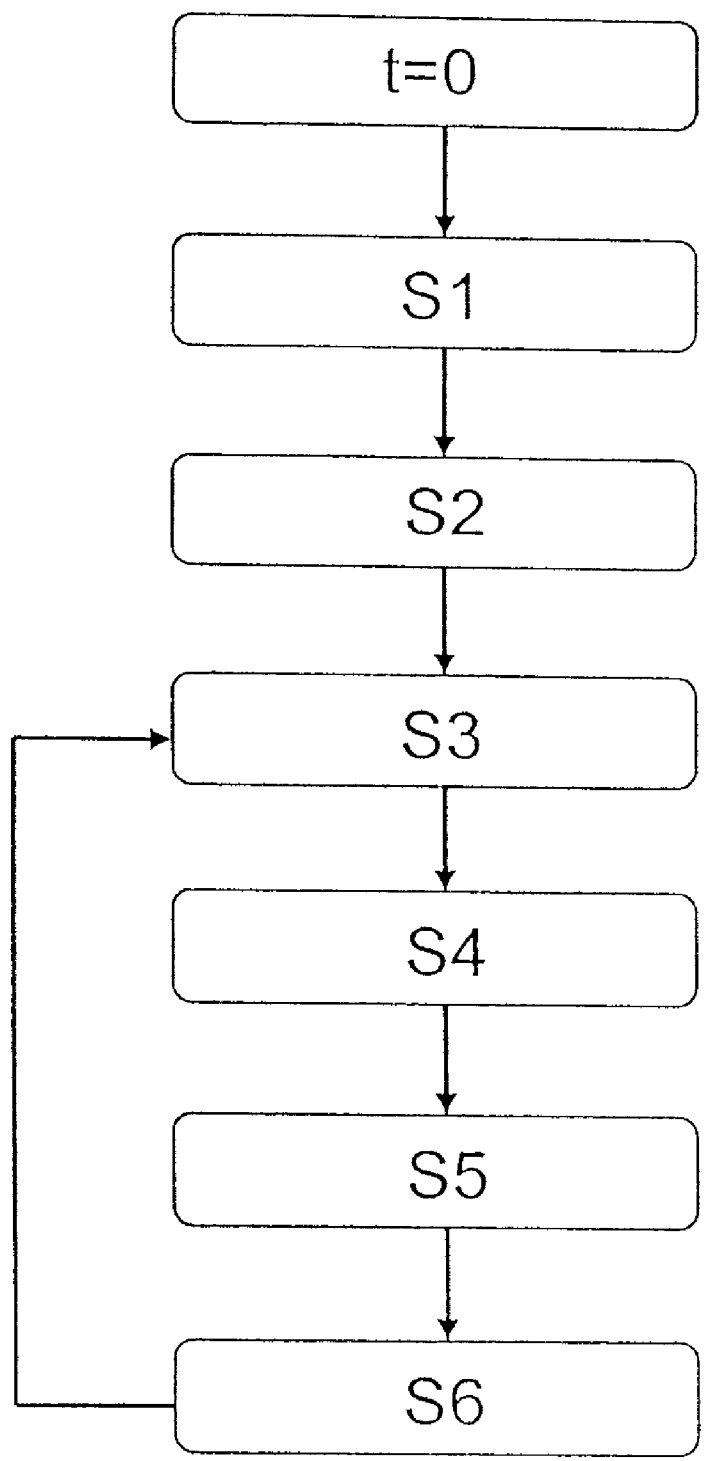
FIG. 4 is a schematic flow chart during the change of the pressure amplitude.

FIG. 4 shows the steps to be taken in an embodiment according to the present invention when changing the pressure amplitude A in a schematic and simplified flow chart. After starting the algorithm shown in FIG. 4 at time t=0, the device 1 is initialized in step S1 with a, for example, preset or currently set amplitude as a start value. The amplitude is outputted in the next step S2. S3 designates a step in which one waits until the amplitude is effectively present on the device 1 and a new measured value for the applied tidal volume is present. A new amplitude is calculated in S4, and this value is optionally clamped or capped in S5, i.e., is set at a value not above a maximum for the pressure amplitude and not below a minimum. The rate of change can now also be limited to a limit. The new amplitude is outputted in step S6 and by returning to step S3, one waits again until the new amplitude becomes effective and a new VT measured value is present.

It is ensured by means of the algorithm shown in FIG. 4 and especially by step S5 in FIG. 4 that the rate of change remains limited or is limited for a change in amplitude and the system is not excited to oscillate or oscillation is advantageously avoided hereby. The rate of change can be set or limited, moreover, by the time constant, which determines the duration of step S3.

Furthermore, another limitation of the rate of change can be brought about in each embodiment by the calculated difference between the set value for VT and the actual value for VT being filtered. The difference is then clamped/capped to the permissible step size. It is only thereafter that the resulting value is used to increase or decrease the amplitude by this value. It is also possible as an alternative to permit only filtration or only to limit the step size.

The algorithm shown in FIG. 4 and especially steps S3 through S6 are taken each time when a new tidal volume VT was determined, even if the pressure amplitude A has not changed.

Figure 5:
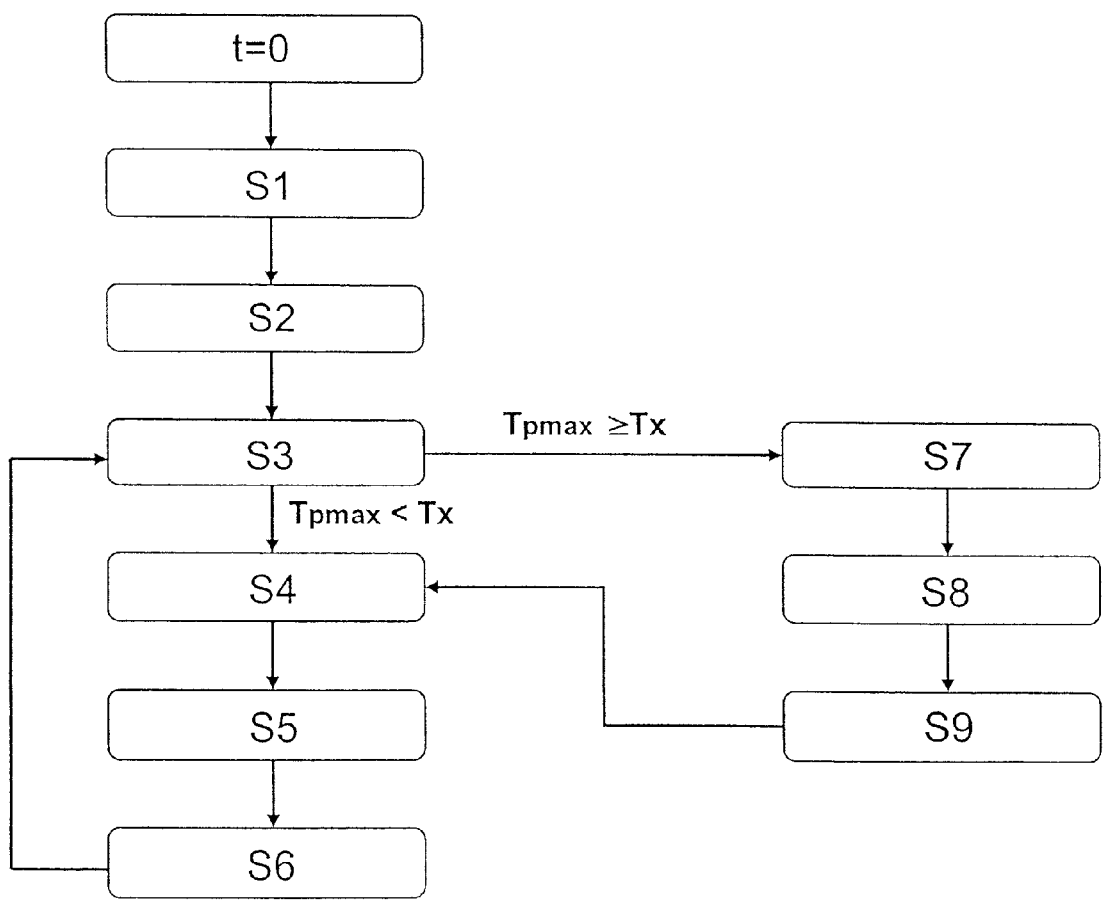
FIG. 5 is a schematic view of the process of a combined amplitude and oscillation frequency change.

FIG. 5 shows the case of another preferred embodiment, in which the respiration pressure is clamped/capped because of the maximum allowable amplitude set or a higher respiration pressure cannot be reached with the current settings (these may be the durations for inspiration and expiration) by means of the given pneumatic system and with the current patient properties (resistance and compliance) and the oscillation frequency is reduced (for example, by one Hz each time). According to the formula (2) given above, the set point or the desired value for the tidal volume VT is increased in order to reach, as before, the oscillation volume necessary for a constant $CO_2$ elimination by means of the device 1. After adjusting the frequency and the tidal volume, it is again necessary to wait until the changes brought about have become established before a new tidal volume measured value can be determined. The algorithm for guaranteeing the respiration volume or to adjust the amplitude, as is shown in FIG. 4, can subsequently be carried out again normally. If the algorithm again approaches pressure limitation, the frequency is reduced stepwise further, doing so until the minimum allowable frequency or the preset tidal volume has been reached. The frequency reduction shall not, moreover, be carried out immediately when reaching the pressure limitation, but only when the pressure limitation has been in effect for some time and it is ascertained as a result that the preset tidal volume cannot indeed be reached at the current frequency. Temporary pressure limitations shall not possibly lead to changes in the frequency.

This purpose is served by the algorithm shown in FIG. 5. Besides the steps S1 through S6 already known from FIG. 4, a polling is made in the algorithm according to FIG. 5 in step S3 to determine whether the pressure limitation has been in effect for a sufficient period of time or not. If the duration $T_{pmax}$ for which the pressure limitation has been present is longer than a certain duration $T_x$, the algorithm passes over to a step S7, in which the frequency is reduced and a new tidal volume set value is calculated. Step S7 is followed by step S8, in which the frequency is clamped or capped, whereupon one waits in step S9 until the frequency is effective and a new tidal volume measured value is present. A new amplitude is subsequently calculated. The algorithm passes for this purpose over from step S9 to step S4.

If there is no pressure limitation or this has been applied since a short time ago only (i.e., when $T_{pmax}<T_x$), the algorithm passes over from step S3 to step S4, as is known from FIG. 4.

FIG. 6 shows a schematic and simplified view of an arrangement according to the present invention as a conceptual abstraction and basis for FIG. 3 with an inspiration source 31, an inspiration valve 33, a flow sensor 25 as well as an expiration valve 35 with ejector.

Thus, the present invention describes, for the first time ever, a device for respirating a patient by means of high-frequency ventilation, which has at least one means for setting a desired tidal volume by a user, and which has at least one regulating means for regulating an amplitude of the respiration pressure and/or at least one regulating means for regulating the oscillation frequency on the basis of the tidal volume determined. The present invention shows, furthermore, a corresponding method for regulating a device for respirating a patient by means of high-frequency ventilation and a method for respirating a patient.

While specific embodiments of the invention have been shown and described in detail to illustrate the application of the principles of the invention, it will be understood that the invention may be embodied otherwise without departing from such principles.

What is claimed is:

1. A device for respirating a patient by means of high-frequency ventilation, the device comprising:
   a high-frequency generator for applying a tidal volume with a respiration pressure with an oscillation frequency;
   tidal volume determination means for determining a tidal volume applied to said patient;
   setting means for setting a desired tidal volume by a user; and
   regulating means for regulating at least one of an amplitude of the respiration pressure and the oscillation frequency on the basis of the determined tidal volume.

2. A device in accordance with claim 1, wherein the desired tidal volume is set by said regulating means for regulating said oscillation frequency such that a product of a second power of said tidal volume and said oscillation frequency remains constant.

3. A device in accordance with claim 2, further comprising respiration pressure amplitude setting means for setting a maximum value for said amplitude of the respiration pressure, wherein a regulation of said oscillation frequency takes place in time after raising said amplitude to a maximum value set.

4. A device in accordance with claim 3, further comprising checking means for checking, before setting said oscillation frequency, whether the maximum value set for said amplitude has been set for at least a predeterminable duration.

5. A device in accordance with claim 1, wherein said regulating means limits a rate of change during the change of said oscillation frequency and/or said amplitude.

6. A method for regulating a device for respirating a patient using high-frequency ventilation, the method comprising the steps of:
   providing a high-frequency generator for applying a tidal volume with a respiration pressure with an oscillation frequency;
   providing a flow sensor for measuring a gas flow applied to said patient and a tidal volume determination means for determining a tidal volume applied to said patient based on the measured gas flow;
   providing a setting means for setting a desired tidal volume by a user;
   providing a regulating means for regulating at least one of an amplitude of the respiration pressure and the oscillation frequency on the basis of the determined tidal volume;
   predetermining a desired tidal volume;
   determining the tidal volume applied to the patient with the tidal volume determination means; and regulating at least one of an amplitude and an oscillation frequency of a respiration pressure on the basis of the determined tidal volume.

7. A method in accordance with claim 6, further comprising:
setting the desired tidal volume during regulation of said oscillation frequency such that a product of a second power of said tidal volume and said oscillation frequency remains constant.

8. A method in accordance with claim 6, further comprising:
setting a maximum value for the amplitude of the respiration pressure; and
setting the desired tidal volume such that regulation of said oscillation frequency takes place in time after raising the amplitude to a maximum value set.

9. A method in accordance with claim 8, further comprising:
checking, before a change is made in said oscillation frequency, whether the setting of the maximum value for said amplitude of the respiration pressure was carried out before a period of time.

10. A method in accordance with claim 6, further comprising:
limiting a rate of change during changes in said oscillation frequency and/or in said amplitude.

11. A method for respirating a patient, the method comprising the steps of:
providing a high-frequency generator for applying a tidal volume with a respiration pressure with an oscillation frequency;
providing a tidal volume determination means for determining a tidal volume applied to said patient;
providing a setting means for setting a desired tidal volume by a user;
providing a regulating means for regulating at least one of an amplitude of the respiration pressure and the oscillation frequency on the basis of the determined tidal volume;
predetermining a desired tidal volume;
determining an actual tidal volume to patient; and
regulating at least one of an amplitude and an oscillation frequency of the respiration pressure on the basis of the determined tidal volume.

12. A method in accordance with claim 11, further comprising:
setting the desired tidal volume during regulation of said oscillation frequency such that a product of a second power of said tidal volume and said oscillation frequency remains constant.

13. A method in accordance with claim 11, further comprising:
setting a maximum value for the amplitude of the respiration pressure; and
setting the desired tidal volume such that regulation of said oscillation frequency takes place in time after raising the amplitude to a maximum value set.

14. A method in accordance with claim 13, further comprising:
checking, before a change is made in said oscillation frequency, whether the setting of the maximum value for said amplitude of the respiration pressure was carried out before a period of time.

15. A method in accordance with claim 11, further comprising:
limiting a rate of change during changes in said oscillation frequency and/or in said amplitude.

16. A device for respirating a patient by means of high-frequency ventilation, the device comprising:
a high-frequency generator for applying a tidal volume with a respiration pressure with an oscillation frequency;
a flow sensor for measuring flow applied to said patient;
tidal volume determination means for determining a tidal volume applied to said patient based on the measured flow applied to said patient;
setting means for setting a desired tidal volume by a user; and
regulating means for regulating at least one of an amplitude of the respiration pressure and the oscillation frequency on the basis of the determined tidal volume and based on the tidal volume determined based on the measured flow applied to said patient measured by the flow sensor.

17. A device in accordance with claim 16, wherein the desired tidal volume is set by said regulating means for regulating said oscillation frequency such that a product of a second power of said tidal volume and said oscillation frequency remains constant.

18. A device in accordance with claim 17, further comprising respiration pressure amplitude setting means for setting a maximum value for said amplitude of the respiration pressure, wherein a regulation of said oscillation frequency takes place in time after raising said amplitude to a maximum value set and said regulating means limits a rate of change during the change of said oscillation frequency and/or said amplitude.

19. A device in accordance with claim 18, further comprising checking means for checking, before setting said oscillation frequency, whether the maximum value set for said amplitude has been set for at least a predeterminable duration.

20. A device in accordance with claim 16, wherein said flow sensor measures inspiration and expiration gas flows.

21. A device according to claim 16, wherein:
the tidal volume determination means includes a volume integrator and the tidal volume applied to said patient based on the measured gas flow is determined by measuring flow applied to the patient with the flow sensor to form a measured flow value, feeding the measured flow value to a volume integrator and calculating an actual value of the tidal volume applied; and
said regulating means changes the pressure amplitude generated by a high-frequency generator corresponding to a difference between the desired tidal volume and the determined tidal volume applied.

22. A method according to claim 6, wherein:
the tidal volume applied to said patient based on the measured gas flow is determined by measuring flow applied to the patient with the flow sensor to form a measured flow value, feeding the measured flow value to a volume integrator and calculating an actual value of the tidal volume applied; and
the regulating of at least one of an amplitude and an oscillation frequency of the respiration pressure on the basis of the determined tidal volume includes changing the pressure amplitude generated by a high-frequency generator corresponding to a difference between the desired tidal volume and the determined tidal volume applied.

* * * * *